US005690937A

United States Patent [19]
Parkin et al.

[11] Patent Number: 5,690,937
[45] Date of Patent: Nov. 25, 1997

[54] TEMPERATURE SENSITIVE CLUSTERED CHANGED-TO-ALANINE MUTANTS OF INFLUENZA VIRUS PB2 GENE

[75] Inventors: Neil T. Parkin, Belmont; Kathleen L. Coelingh, San Francisco, both of Calif.

[73] Assignee: Aviron, Mountain View, Calif.

[21] Appl. No.: 462,388

[22] Filed: Jun. 5, 1995

[51] Int. Cl.$^6$ .......................... A61K 39/145; C12N 7/04; C12N 15/44
[52] U.S. Cl. .................................. 424/199.1; 424/209.1; 435/236; 536/23.72
[58] Field of Search .................. 435/320.1, 236; 424/199.1, 209.1; 530/350; 536/23.72

[56] References Cited

FOREIGN PATENT DOCUMENTS

WO 95/08634  3/1995  WIPO.

OTHER PUBLICATIONS

"Intracellular Localization of the Viral Polymerase Proteins in Cells ...", Akkina etal., *Journal of Virology*, Jul. 1987, pp. 2217–2224.
"Two Signals Mediate Nuclear Localization of Influenza Virus ...", Mukaigawa etal., *Journal of Virology*, Jan. 1991, pp. 245–253.
"Complex Structure of the Nuclear Translocation Signal of Influenza Virus ...", Nieto etal., *Journal of General Virology (1994)*, vol. 75, pp. 29–36.
"Molecular Cloning and Sequencing of Influenza Virus ...", S. de la Luna etal., *Virus Research*, vol. 13, (1989), pp. 143–156.
"The RNA Polymerase PB2 Subunit Is Not Required for Replication of the Influenza ...", Nakagawa etal., *Journal of Virology*, Feb. 1995, pp. 728–733.
Abstract: The epidemiology of Guillain–Barre Syndrome (GBS), Schonberger, *Annals of Neurology*, 1981, 9 Suppl:31–8.
"Use of Live Attenuated Cold–Adapted Influenza a Reassortant Virus Vaccines in Infants, Children, Young Adults, and Elderly Adults", B. Murphy, *Infectious Diseases in Clinical Practice* (1993) vol. 2: pp. 174–181.
"Genetic Approaches to the Prevention of Influenza A Virus Infection," Murphy etal., *Genetic Variation Among Influenza Viruses*, pp. 600–614 (1981).
"Genetic Approaches to Attenuation of Influenza A Viruses for Man", Murphy etal., *Phil Trans. R. Soc. Lond.*, B 288, pp. 401–415 (1980).
"Escape of a Highly Defective Influenza A Virus Mutant From Its Temperature," Murphy etal., *Annals New York Academy of Sciences* (1980), pp. 172–182.
"Evaluation of a Phenotypic Revertant of the A/Alaska/ 77–ts–1A2 Reassortant Virus in Hamsters ...", Tolpin etal., *Infection and Immunity*, May 1982, pp. 645–650.
"Evolution of Influenza A Virus PB2 Genes", Gormon etal., *Journal of Virology*, Oct. 1990, pp. 4893–4902.
"Identification of Sequence Changes in the Cold–Adapted ...", Cox etal., *Virology*, vol. 167 (1988), pp. 554–567.

"Molecular and Biological Changes in the Cold–Adapted Master Strain ...", Herlocher etal., *Proc. Natl. Acad. Sci.*, vol. 90, pp. 6032–6036, Jul. 1993.
"Four Viral Genes Independently Contribute to Attenuation of Live Influenza ...", Snyder etal., *Journal of Virology*, Feb. 1988, pp. 488–495, vol. 62, No. 2.
"The critical cut–off temperature of avian influenza viruses," McCauley etal., *Virus Research*, vol. 17, pp. 191–198.
"Characterization of a temparture–sensitive mutant in the RNA polymerase PB2 ...," Yamanaka etal., *Arch. Virol* (1990), vol. 114, pp. 65–73.
"Introduction of site–specific mutations into the genome of influenza virus," Enami etal., *Proc. Natl. Acad. Sci. USA*, vol. 87, pp. 3802–3805.
"High–Efficiency Formation of Influenza Virus Transfectants," Enami etal., *Journal of Virology*, 65:2711–2713, May 1991.
"Amplification, Expression and Packaging of a Foreign Gene by Influenza Virus," Luytjes etal., *Cell*, vol. 59, pp. 1107–1113, Dec. 22, 1989.
"Rescue of an Influenza A Virus Wild–Type PB2 Gene and a Mutant Derivative Bearing ...," Subbara etal., *Journal of Virology*, 67:7223–7228, Dec. 1993.
"Reverse Genetics Provides Direct Evidence for a Correlation of ...," Horimoto etal., *Journal of Virology*, 66:3120–3125, May 1994.
"Influenza A Virus Transfectants with Chimeric Hemagglutinins," Schulman etal., *Journal of Virology*, 66:399–404, Jan. 1992.
"Influenza B Viruses with Site–Specific Mutations Introduced Into ..," Barclay etal., *Journal of Virology*, Feb. 1995, pp. 1275–1279.
"Growth Control of Influenza A Virus by M1 Protein ...," Yasuda etal., *Journal of Virology*, 68:8141–8146, Dec. 1994.
"A Systematic Mutational Analysis of Hormone–Binding Determinants in the ...," Bass etal., *Proc. Natl. Acad. Sci., USA*, vol. 88, pp. 4498–4502, May 1991.
"Systematic Mutational Analysis of the Yeast ACTI Gene ...," Wertman etal., *Genetics*, pp. 337–350 (1995).
"Clustered Charged–to–Alanine Mutagenesis ...," by Diamond etal., *Journal of Virology*, 68:863–876, Feb. 1994.
"Targeted Construction of Temperature–Sensitive ...," Hassett etal., *Proc. Natl., Acad. Sci.*, vol. 91, pp. 4554–4558 (1994).
"Identification and Characterization of a Temperature–Sensitive Mutant of Human ...," Wiskerchen, *Journal of Virology*, 69:597–601, Jan. 1991–601.

(List continued on next page.)

*Primary Examiner*—George C. Elliott
*Assistant Examiner*—Terry A. McKelvey
*Attorney, Agent, or Firm*—Luann Cserr; Tracy Dunn

[57] ABSTRACT

Recombinant PB2 variant influenza viruses, RNA, cDNA and vectors are provided. Also provided are immunogenic compositions containing the variant viruses, methods of producing such viruses and methods for the prophylactic treatment of influenza in humans.

4 Claims, No Drawings

OTHER PUBLICATIONS

"Use of Single–Gene Ressortant Viruses to Study the Role of Avian Influenza A . . . ," Clements etal., *Journal of Clinical Microbiology*, 30:655–662, Mar. 1992.

"Nucleotide Sequence Changes in the Polymerase Basic Protein 2 games," Lawson et al., *Virology*, Vo. 191, pp. 506–510.

Baylor, "Transient Expression and Sequence of the Matrix ($M_1$) Gene of WSN Influenza A Virus in a Vaccinia Vector", *Virology*, 163: 618–621 (1988).

Markushin, "Nucleotide sequence of RNA segment 7 and the predicted amino sequence of M1 and M2 proteins of FPV/Weybridge (H7N7) and WSN (H1N1) influenza viruses", *Virus Research*, 10, (1988) 263–272.

Buckler–White, "Characterization of a Gene Coding for M Proteins Which Is Involved in Host Range Restriction of an Avian Influenza A Virus in Monkeys", *Journal of Virology*, Feb. 1986, pp. 697–700.

Shu, "Analysis of the Evolution and Variation of the Human Influenza A Virus Nucleoprotein Gene from 1933 to 1990", *Journal of Virology*, May 1993, pp. 2723–2729, vol. 67, No. 5.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
      ( A ) LENGTH: 56 bases
      ( B ) TYPE: nucleic acid
      ( C ) STRANDEDNESS: single
      ( D ) TOPOLOGY: linear ( i i ) MOLECULE TYPE: SYNTHETIC DNA ( i x ) FEATURE:
  ( A ) NAME/KEY: PB2002

( x ) SEQUENCE DESCRIPTION: SEQ ID NO:1:

GCGCGCTCTA GAATTAACCC TCACTAAAAG TAGAAACAAG GTCGTTTTTA AACTAT    56

( 2 ) INFORMATION FOR SEQ ID NO:2:

( i ) SEQUENCE CHARACTERISTICS:
    ( A ) LENGTH: 43 bases
    ( B ) TYPE: nucleic acid
    ( C ) STRANDEDNESS: single
    ( D ) TOPOLOGY: linear ( i i ) MOLECULE TYPE: SYNTHETIC DNA ( i x ) FEATURE:
    ( A ) NAME/KEY: PB2003

( x ) SEQUENCE DESCRIPTION: SEQ ID NO:2:

GCGCGCGGAT CCGAATGCGA GCAAAAGCAG GTCAATTATA TTC    43

( 2 ) INFORMATION FOR SEQ ID NO:3:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( i i ) MOLECULE TYPE: SYNTHETIC DNA ( i x ) FEATURE:
    ( A ) NAME/KEY: PB2004

( x ) SEQUENCE DESCRIPTION: SEQ ID NO:3:

GGGAAAAGGG CAACAGCTAT A    21

( 2 ) INFORMATION FOR SEQ ID NO:4:

( i ) SEQUENCE CHARACTERISTICS:
    ( A ) LENGTH: 20 bases
    ( B ) TYPE: nucleic acid
    ( C ) STRANDEDNESS: single
    ( D ) TOPOLOGY: linear ( i i ) MOLECULE TYPE: SYNTHETIC DNA ( i x ) FEATURE:
    ( A ) NAME/KEY: PB2005

( x ) SEQUENCE DESCRIPTION: SEQ ID NO:4:

CACCTCTAAC TGCTTTTATC    20

( 2 ) INFORMATION FOR SEQ ID NO:5:

( i ) SEQUENCE CHARACTERISTICS:
    ( A ) LENGTH: 19 bases
    ( B ) TYPE: nucleic acid
    ( C ) STRANDEDNESS: single
    ( D ) TOPOLOGY: linear ( i i ) MOLECULE TYPE: SYNTHETIC DNA ( i x ) FEATURE:
    ( A ) NAME/KEY: PB2006

( x ) SEQUENCE DESCRIPTION: SEQ ID NO:5:

GAAAAAGCAC TTTTGCATC    19

( 2 ) INFORMATION FOR SEQ ID NO:6:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: SYNTHETIC DNA ( i x ) FEATURE:
        ( A ) NAME/KEY: n2pb2.4

( x ) SEQUENCE DESCRIPTION: SEQ ID NO:6:

AAGAGCCACA GTATCAGCAG                        20

( 2 ) INFORMATION FOR SEQ ID NO:7:

( i ) SEQUENCE CHARACTERISTICS:
        ( A ) LENGTH: 62 bases
        ( B ) TYPE: nucleic acid
        ( C ) STRANDEDNESS: single
        ( D ) TOPOLOGY: linear ( i i ) MOLECULE TYPE: SYNTHETIC DNA ( i x ) FEATURE:
        ( A ) NAME/KEY: ALA1

( x ) SEQUENCE DESCRIPTION: SEQ ID NO:7:

GTATCTCGCG AGTGCGAGAC TGCGACATCA GGTTCCGTAG TTCAGCTATA GCTTCCATAC 60

TG                                                                                    62

( 2 ) INFORMATION FOR SEQ ID NO:8:

( i ) SEQUENCE CHARACTERISTICS:
        ( A ) LENGTH: 46 bases
        ( B ) TYPE: nucleic acid
        ( C ) STRANDEDNESS: single
        ( D ) TOPOLOGY: linear ( i i ) MOLECULE TYPE: SYNTHETIC DNA ( i x ) FEATURE:
        ( A ) NAME/KEY: ALA2

( x ) SEQUENCE DESCRIPTION: SEQ ID NO:8:

GGTTCCATGT TTTAAAGCTT CAACAGCGTC AAAATAAGTC TTGTAG          46

( 2 ) INFORMATION FOR SEQ ID NO:9:

( i ) SEQUENCE CHARACTERISTICS:
        ( A ) LENGTH: 43 bases
        ( B ) TYPE: nucleic acid
        ( C ) STRANDEDNESS: single
        ( D ) TOPOLOGY: linear ( i i ) MOLECULE TYPE: SYNTHETIC RNA ( i x ) FEATURE:
        ( A ) NAME/KEY: ALA3

( x ) SEQUENCE DESCRIPTION: SEQ ID NO:9:

CCAGGGTTTA TGTCTACAGC TGCGGCTATT TTGACTTGAT TTC             43

( 2 ) INFORMATION FOR SEQ ID NO:10:

( i ) SEQUENCE CHARACTERISTICS:
        ( A ) LENGTH: 45 base pairs (B) TYPE: nucleic acid
(C) STRANDEDNESS: single
(D) TOPOLOGY: linear (ii) MOLECULE TYPE: SYNTHETIC RNA (ix) FEATURE:
    (A) NAME/KEY: ALA4

(x) SEQUENCE DESCRIPTION: SEQ ID NO:10:

GCAATCTCGG AGTTCTTCAG CTGCCTCTTT GGTTATTGTT AATTG                45

(2) INFORMATION FOR SEQ ID NO:11:

(i) SEQUENCE CHARACTERISTICS:
    (A) LENGTH: 44 bases
    (B) TYPE: nucleic acid
    (C) STRANDEDNESS: single
    (D) TOPOLOGY: linear (ii) MOLECULE TYPE: SYNTHETIC RNA (ix) FEATURE:
    (A) NAME/KEY: ALA5

(x) SEQUENCE DESCRIPTION: SEQ ID NO:11:

CAAGCGGGTC CTCAATCGCA GCTGAGGAAG AAGTGCTTAC AGGC                 44

(2) INFORMATION FOR SEQ ID NO:12:

(i) SEQUENCE CHARACTERISTICS:
    (A) LENGTH: 38 bases
    (B) TYPE: nucleic acid
    (C) STRANDEDNESS: single
    (D) TOPOLOGY: linear (ii) MOLECULE TYPE: SYNTHETIC RNA (ix) FEATURE:
    (A) NAME/KEY: ALA6

(x) SEQUENCE DESCRIPTION: SEQ ID NO:12:

CCGGATGTGC TTGCAGCTGG GGCTTCAATT AAAGTGCC                        38

(2) INFORMATION FOR SEQ ID NO:13:

(i) SEQUENCE CHARACTERISTICS:
    (A) LENGTH: 39 bases
    (B) TYPE: nucleic acid
    (C) STRANDEDNESS: single
    (D) TOPOLOGY: linear (ii) MOLECULE TYPE: SYNTHETIC RNA (ix) FEATURE:
    (A) NAME/KEY: ALA7

(x) SEQUENCE DESCRIPTION: SEQ ID NO:13:

GCTTAATGCT GGTCCGTACG CTGCGTCTTC CTTACCTAG                       39

(2) INFORMATION FOR SEQ ID NO:14:

(i) SEQUENCE CHARACTERISTICS:
    (A) LENGTH: 37 bases
    (B) TYPE: nucleic acid
    (C) STRANDEDNESS: single
    (D) TOPOLOGY: linear (ii) MOLECULE TYPE: SYNTHETIC RNA (ix) FEATURE:
    (A) NAME/KEY: ALA8

( x ) SEQUENCE DESCRIPTION: SEQ ID NO:14:

GCTAGAGTCC CGTTTTCTGG CCATTACCAA CACCACG        37

TEMPERATURE SENSITIVE CLUSTERED CHANGED-TO-ALANINE MUTANTS OF INFLUENZA VIRUS PB2 GENE

FIELD OF THE INVENTION

This invention relates to influenza virus immunogenic compositions and methods of producing such compositions. More specifically, this invention relates to influenza virus immunogenic compositions having discreet, specifically engineered mutations in the PB2 polymerase RNA sequence of influenza.

BACKGROUND

Influenza is an enveloped, single-stranded, negative-sense RNA virus that causes serious respiratory ailments throughout the word. It is the only member of the Orthomyxoviridae family and has been subgrouped into three types, A, B and C.

Influenza virions consist of an internal ribonucleoprotein core containing the single-stranded RNA genome and an outer lipoprotein envelope lined inside by a matrix (hereinafter "M1") protein. The segmented genome of influenza A consists of eight molecules of linear, negative polarity, single-stranded RNA sequences that encode ten polypeptides. Segment 1 is 2341 nucleotides in length and encodes PB2, a 759 amino acid polypeptide which is one of the three proteins which comprise the RNA-dependent RNA polymerase complex. The remaining two polymerase proteins, PB1, a 757 amino acid polypeptide, and PA, a 716 amino acid polypeptide, are encoded by a 2341 nucleotide sequence and a 2233 nucleotide sequence (segments 2 and 3), respectively. Segment 4 of the genome consists of a 1778 nucleotide sequence encoding a 566 amino acid hemagglutin (HA) surface glycoprotein which projects from the lipoprotein envelope and mediates attachment to and entry into cells. Segment 5 consists of 1565 nucleotides encoding a 498 amino acid nucleoprotein (NP) protein that forms the nucleocapsid. Segment 6 consists of a 1413 nucleotide sequence encoding a 454 amino acid neuraminidase (NA) envelope glycoprotein. Segment 7 consists of a 1027 nucleotide sequence encoding a 252 amino acid M1 protein, and a 96 amino acid M2 protein, which is translated from a spliced variant of the M RNA. Segment 8 consists of a 890 nucleotide sequence encoding two nonstructural proteins, NS1 and NS2, composed of 230 and 121 amino acids respectively, whose function is not well defined. NS2 is translated from a spliced variant of the NS RNA.

The segmented genome of influenza B consists of eight molecules of linear, negative polarity, single-stranded RNA sequences that encode eleven polypeptides. Segment 2 is 2396 nucleotides in length and encodes PB2, a 770 amino acid polypeptide which is one of the three RNA-dependent RNA polymerase proteins. The remaining two influenza B polymerase proteins, PB1, a 752 amino acid polypeptide, and PA, a 725 amino acid polypeptide, are encoded by a 2386 nucleotide sequence and a 2304 nucleotide sequence (segments 1 and 3), respectively. Segment 4 of the genome consists of a 1882 nucleotide sequence encoding a 584 amino acid HA surface glycoprotein which projects from the lipoprotein envelope and mediates attachment to cells and membrane fusion. Segment 5 consists of 1839–1841 nucleotides encoding a 560 amino acid NP protein that forms the nucleocapsid. Segment 6 consists of a 1454 nucleotide sequence encoding a 466 amino acid NA envelope glycoprotein and a 100 amino acid NB protein, a nonstructural protein whose function is unknown. Segment 7 consists of a 1191 nucleotide sequence encoding a 248 amino acid M1 protein and a 195 amino acid BM2 protein which is translated from a separate reading frame. Segment 8 consists of a 1096 nucleotide sequence encoding nonstructural proteins NS1 and NS2, composed of 281 and 122 amino acids respectively, whose functions are not well defined. NS2 is translated from a spliced variant of the NS RNA.

The segmented genome of influenza C consists of seven molecules of linear, negative polarity, single-stranded RNA sequences that encode eight polypeptides. Segment 1 is 2365 nucleotides in length and encodes PB2, a 774 amino acid polypeptide which is one of the three RNA-dependent RNA polymerase proteins. The remaining two polymerase proteins, PB1, a 754 amino acid polypeptide, and PA, a 709 amino acid polypeptide, are encoded by a 2363 nucleotide sequence and a 2183 nucleotide sequence (segments 2 and 3), respectively. Segment 4 of the genome consists of a 2074 nucleotide sequence encoding a 655 amino acid hemagglutinin-esterase surface glycoprotein which projects from the lipoprotein envelope and mediates attachment to cells, fusion, and has receptor-destroying activities. Segment 5 consists of a 1809 nucleotide sequence encoding a 565 amino acid NP protein that forms the nucleocapsid. Segment 6 consists of a 1180 nucleotide sequence encoding a 374 amino acid matrix (M) protein. Segment 7 consists of a 934 nucleotide sequence encoding a 286 amino acid NS1 protein, and a 122 amino acid NS2 protein, which is translated from a spliced variant of the NS RNA.

To infect a cell influenza HA protein adsorbs to sialyloligosaccharide molecules in cell membrane glycoproteins and glycolipids. Following endocytosis of the virion, a conformational change in the HA molecule occurs within the cellular endosome that facilitates membrane fusion and triggers uncoating. The nucleocapsid migrates to the nucleus where viral mRNA is transcribed as the essential initial event in infection. Transcription and replication of influenza RNA take place in the nucleus of infected cells and assembly into virions occurs by budding out of or through the plasma membrane. The viruses can reassort genes during mixed infections.

Replication of influenza virus RNAs is dependent on four viral gene products: PB1, PB2, PA, and NP. The three polymerase proteins, PB1, PB2, and PA, form a trimolecular complex in the nuclei of infected cells. Each protein has its own nuclear localization signal. See Akkina, *J Virol* 61:2217–24 (1987), Mukaigawa, *J Virol* 65:245–253 (1991) and Nieto, *J Gen Virol* 75:29–36 (1994). Some specific functions have been ascribed to the individual polypeptides. PB1 appears to be primarily involved in the enzymatic polymerization process, i.e. the elongation step. It shares regions of amino acid homology with other RNA-dependent RNA polymerase proteins. The precise function of PA is unknown. The PB2 protein binds to the 5'-terminal cap structure present on host cell mRNAs; the mRNAs are then cleaved, producing a capped 9 to 15-mer oligoribonucleotide which serves as a primer for transcription of influenza mRNAs. The PB2 amino acid sequence contains a region of limited homology with the cellular cap-binding protein, eIF-4E. See de la Luna, *Virus Res* 13:143–56 (1989). While PB2 is not absolutely required for replication of viral RNA, mRNAs transcribed from viral template in cells expressing only PB1, PA, and NP are uncapped and thus cannot be translated. See Nakagawa, *J Virol* 69:728–33 (1995). Transcripts terminate at sites 15–22 bases from the ends of their templates, where oligo(U) sequences act as signals for the template-independent addition of poly(A) tracts. At a later stage of infection, instead of making mRNAs, the polymerase proteins PB1, PB2 and PA are used to make new viral RNA genomes. The polymerase complex first transcribes cRNA, which then serves as template for production of more vRNA. The plus-stranded cRNA copies differ from the plus-stranded mRNA transcripts by lacking capped and methylated 5'-termini. Also, they are not truncated or polyadenylated at the 3' termini. Thus, the cRNAs are coterminal with their negative strand templates and contain all the genetic information in each genomic segment in the complementary form.

The negative strand genomes (vRNAs) and antigenomes (cRNAs) are always encapsidated by viral nucleocapsid proteins; the only unencapsidated RNA species are virus mRNAs. Nucleocapsid assembly appears to take place in the nucleus. The virus matures by budding from the apical surface of the cell incorporating the M1 protein on the cytoplasmic side or inner surface of the budding envelope. The HA and NA glycoproteins are incorporated into the lipid envelope. In permissive cells, HA is post-translationally cleaved, but the two resulting chains remain associated by disulfide bonds.

Efforts to produce immunogenic compositions against influenza have taken two paths. Inactive vaccines, which cannot replicate in the host, can be either chemically inactivated whole virus or vital subunit proteins. Both inactivated and subunit virus vaccines are available for influenza. These vaccines contain the HA and NA surface proteins as antigens which give rise to the immune response upon administration to the host. For reasons which are incompletely understood, subunit vaccines have exhibited an efficacy of only 60% to 80% against influenza disease. Inactivated whole virus vaccines are administered intramuscularly and primarily stimulate a systemic immune response, whereas live attenuated vaccines also stimulate local mucosal immunity. The latter form of immunity is more effective since it is present in the upper respiratory tract where the virus is first encountered. Also, inactivated vaccines typically have reduced ability to induce cytotoxic T cell responses, and can sometimes cause delayed hypersensitivity reactions. Guillain-Barre syndrome has been associated with the inactivated influenza A "swine flu" vaccine. See, Schonberger, *Ann Neurol 9(supp):*31–38(1981).

Live attenuated viruses can be employed in immunogenic compositions and are typically successful at inducing the required protective response in the host. Live attenuated influenza viruses are capable of limited replication in the host, thus stimulating a protective immune response, but without causing disease. Previously, such mutants have been generated by multiple passage through an unnatural host such as embryonated chicken eggs, by successive passage through an unnatural host at increasingly lower temperatures, or by random mutagenesis via chemical methods and selection of conditional mutants. These methods can result in the loss of pathogenicity while retaining immunogenicity. However, the identity of the genetic mutations generated as described above are unknown a priori and when the mutant "master donor" virus is selected as a vaccine candidate. If such mutations are limited to one or two nucleotide changes, the virus composition could ultimately "revert" or back mutate in the host and thus regain its original pathogenic phenotype. However, one of these methods, successive passage at increasingly lower temperatures, has given rise to a virus (the "cold-adapted" strain derived from A/Ann Arbor/6/60) with multiple mutations that has been shown to be genetically stable. See Murphy, *Inf Dis In Clin Practice* 2:174–181 (1993). In making such vaccine compositions, the HA and NA RNA sequences of the attenuated master donor virus are replaced with HA and NA RNA sequences from circulating influenza strains. Such viruses are termed reassortant viruses.

Temperature sensitive (ts) mutants of influenza, generated by chemical mutagenesis or identified by screening for spontaneous mutants have been described. Such mutants are unable to replicate in the lower respiratory tract of infected animals and often replicate in the upper respiratory tract to a lower level than wild-type virus. One of these mutants, ts1A2, was shown to have many of the desired characteristics of a live attenuated influenza vaccine. See Murphy and Chanock, Genetic Variation Among Influenza Viruses, pps 601–615, Nayak, D.ed, Academic Press, N.Y. (1981) and Murphy, *Phil Trans R Soc Lon B* 288:401–15(1980). The ts1A2 strain was found to contain temperature sensitive lesions in both PB1 and PB2, and exhibited the desired level of attenuation but was genetically unstable and reverted to a virulent state after replication in a seronegative young vaccinee. See Murphy, *Ann NY Acad Sci* 354:172–82 (1980) and Tolpin, *Infection and Immunity* 36:645–50 (1982).

A panel of temperature sensitive mutants of the A/Udorn/307/72 whose ts lesions were mapped to the PB2 gene has been described. Sequence analysis led to the discovery of mutations at amino acid positions 65, 100, 112, 171, 298, 310, 386, 391 and 556 of PB2. Similarly, the PB2 gene of the ts1A2 virus was found to have a mutation at amino acid position 658. See Lawson, *Virology* 191:506–10 (1992). The cold-adapted strain of A/AA/6/60 is also temperature sensitive and sequence analysis has suggested that one of the mutations which may be partly responsible for the ts phenotype is an asparagine to serine change at amino acid position 265 of PB2. See Cox, *Virology* 167:554–67 (1988), Herlocher, *Proc Natl Acad Sci* 90:6032–36 (1993) and Snyder, *J Virol* 62:488–95 (1988). Additionally, PB2 ts mutants of A/WSN/33 and of A/FPV/Rostock/34 are known. The mutation in the PB2 gene sequence, presumably responsible for the ts phenotype, was localized to amino acid 417 in the case of A/WSN/33 and to amino acid 512 in the case of A/FPV/Rostock/34. See McCauley, *Virus Res* 17:191–98 (1990) and Yamanaka, *Arch Virol* 114:65–73 (1990). Collectively, these studies suggest many potential sites in the PB2 protein where mutations may be introduced in order to generate a ts virus.

An alternate method of creating a live attenuated virus is by employing the techniques of "reverse genetics". See Enami, *Proc Natl Acad Sci* 87:3802–05(1990), Enami and Palese, *J Virol* 65:2711–13(1991) and Luytjes, *Cell* 59:1107–13 (1989). In this process, modified vRNA-like transcripts are transcribed in vitro from cDNA constructs in the presence of purified NP, PB1, PB2, and PA proteins. The resulting synthetic RNP is then transfected into cells previously infected with influenza virus, usually a helper virus which has a conditional growth defect, such as host range restriction or temperature sensitivity, which allows the subsequent selection of transfectant viruses. For example, host-range helper viruses have been successfully used to rescue synthetic NA and PB2 genes. See Enami, supra, and Subbarao, *J Virol* 67:7223–7228 (1993). Antibody selection can also be used to select transfectants in the case of the HA and NA genes. Using antibody selection techniques, the surface HA glycoprotein gene has been transfected and rescued into influenza A virus. See, Horimoto and Kawaoka, *J Virol* 68:3120–3128 (1994) and Li, *J Virol* 66:399–404 (1992). The HA gene has also been transfected and rescued into influenza B virus. See, Barclay and Palese, *J Virol* 69:1275–1279 (1995). The M gene (see, Yasuda, *J Virol.* 68:8141–8146 (1994)), and the NP gene (see Li, *Virus Res.*, in press), has also been rescued using the techniques of reverse genetics.

Given the possibility of using reverse genetics to engineer specific mutations into the genome of influenza, it should be possible to create a ts strain with mutations that are less likely to revert and thus exhibit the desired property of genetic stability. This may be accomplished by introducing new codons which would require more than one nucleotide within the codon to mutate in order to encode the wild-type amino acid, by mutating sites which are less likely to be suppressed extragenically, or by introducing multiple, independently-acting mutations in one or more genes. Since only four of the amino acid changes described above can be engineered such that more than one base change is required in order to revert to a codon that encodes the wild-type amino acid, the identification of additional sites for the introduction of ts mutations would be highly desirable.

"Clustered charged-to-alanine mutagenesis" is a technique whereby charged amino acids are mutagenized to the uncharged amino acid alanine so as to maintain the overall structure or stability of the protein while modifying its bioactivity. It has been used to create mutants of the human growth hormone receptor protein (see Bass, *Proc Natl Acad Sci* 88:4498–4502 (1991)), the *Saccharomyces cervisiae* actin protein (see Wertman, *Genetics* 132:337–50 (1995)), the poliovirus 3D polymerase protein (see Diamond and Kirkegaard, *J Virol* 68:863–76 (1994)), the vaccinia virus G2R protein (see Hassett and Condit, *Proc Natl Acad Sci* 91:4554–4559 (1994)), and human immunodeficiency virus type 1 integrase protein (see Wiskerchen, *J Virol* 69:597–601 (1995)). In each of the foregoing cases, a "charged cluster" was defined as a sequence of five contiguous amino acids, at least two of which are charged.

SUMMARY OF THE INVENTION

We have found that modification of clustered charged amino acid residues in a native protein of influenza results in the consistent, predictable, exhibition of temperature sensitivity in influenza virus. "Clustered charged amino acid residues", as defined herein with respect to influenza virus, means a sequence of at least five consecutive amino acids in a native protein of an influenza virus comprised of four or five positively or negatively charged amino acids. Charged amino acids (positive or negative) include arginine, lysine, aspartic acid, glutamic acid and histidine. The invention is exemplified by its demonstration using the influenza PB2 protein.

Accordingly, in one aspect the invention comprises novel PB2 variant polypeptide sequences and RNA sequences encoding PB2 variant polypeptides, which, when incorporated into influenza viral master donor viruses, cause such viruses to exhibit a temperature sensitive phenotype.

The PB2 variant RNA sequences can be rescued into influenza genomes to create such influenza master donor virus strains containing the specific temperature sensitivity inducing mutations desired using the techniques of reverse genetics. Thus, in another aspect the invention comprises recombinant influenza viruses containing such novel PB2 variant RNA and polypeptide sequences. These recombinant influenza viruses cause attenuated growth in cultured cells and/or live hosts and are useful as master donor viruses in the preparation of influenza virus reassortants and immunogenic compositions for the prophylactic treatment of humans for influenza infection. To make such recombinant influenza viruses, permissive host cells are infected with a helper virus and transfected with a synthetic RNP complex. The synthetic RNP complex is transcribed in vitro from DNA that encodes the mutated RNA sequence and packaged into ribonucleoprotein (RNP) before transfection. Viral progeny resulting from the transfection includes virus that has incorporated the mutated, transfected RNA sequence into viral particles. Transfectant viruses recovered from the cells that have incorporated the mutated, transfected sequence are then selected from the mixture of transfectant and helper virus, exploiting a phenotypic difference between the two viruses. These transfectant viruses so selected comprise the recombinant influenza viruses of the invention. In a preferred embodiment, the mutated sequence is an influenza PB2 sequence and/or an influenza M sequence and/or an influenza NP sequence. In such embodiments, the mutated PB2 and/or M sequence and/or NP sequence will contain temperature-sensitive mutations giving rise to attenuating phenotypes.

In yet another aspect the invention comprises a method of producing modifications in an influenza genome comprising introducing a recombinant, negative strand RNA template encoding a PB2 variant protein having charged cluster mutations into cells infected with a helper virus capable of producing influenza virus RNA segments. One helper virus which can be employed is capable of growth in avian cells but not in mammalian cells. More specifically for example, Madin-Darby bovine kidney (MDBK) cells can be infected with a host-range mutant of influenza containing the PB2 gene of the avian virus. See Clements, *J Clin Microbiol* 30:655–662 (1992). Synthetic PB2 RNP is then prepared in vitro by transcription of a cDNA template encoding the mutated, vRNA-sense, PB2 RNA in the presence of purified RNP proteins. The cDNA must encode a PB2 protein which, when rescued into the helper virus, allow it to form plaques in mammalian cells. The resulting RNP is introduced into the infected MDBK cells, the cells incubated and the medium harvested and used to infect MDCK cells.

In yet another aspect, the invention comprises a reassortant virus including RNA sequences encoding the HA and NA glycoproteins derived from a wide-type epidemic strain of influenza virus, and the remaining RNA sequences derived from the transfectant virus. The wide-type epidemic virus is a circulating strain of influenza virus against which immunity is desired. The transfectant virus is the attenuated master donor, i.e. recombinant influenza virus of the invention which contains attenuating mutations in one or more of the RNA segments encoding the internal proteins, preferably the cluster charged modifications in the PB2 sequences of the invention as disclosed herein and/or cluster charged modifications of the M sequence which can be created and tested for attenuation following the methods described herein. The most reproducible way to generate a suitably attenuated vaccine virus is to retain all six of the internal protein RNA segments (PB1, PB2, PA, NP, M, and NS) of the master donor; however, it may also be possible to have fewer master donor segments in the vaccine virus but still maintain an appropriate level of attenuation, and genetic stability.

In yet another aspect, the invention comprises immunogenic pharmaceutical compositions containing an immunogenically-inducing effective amount of an influenza virus variant in admixture with a pharmaceutically acceptable carrier or solution.

In yet another aspect the invention comprises a method for the prophylactic treatment of a patient comprising administering an immunogenically-inducing effective amount of an immunogenic pharmaceutical composition of the invention to such patient. By "immunogenically-inducing" we mean an amount sufficient for stimulating in a mammal the production of protective antibodies to influenza. Such an amount may stimulate antibody production locally and/or systemically, thereby preventing infection or the disease caused by such infection. Preferably, the patient is a human patient.

DETAILED DESCRIPTION OF THE INVENTION

In this disclosure, reference is made to the common amino acids using the conventional single-letter symbols.

The modification of clustered charged amino acid residues in influenza results in the consistent and predictable exhibition of temperature sensitivity in the virus. By "charged clusters" "cluster charged" or "clustered charged amino acid residues" we mean a sequence of at least five consecutive amino acids comprised of four or five positively or negatively charged amino acids in the native proteins of influenza. Charged amino acids include the following: arginine, lysine, aspartic acid, glutamic acid and histidine.

Eight charged clusters of amino acid residues were identified in the influenza A virus A/LA/2/87 PB2 protein. These charged clusters comprised amino acids 2 through 6 (referred to in the experimental section as "ALA1"), 120 through 124 ("ALA2"), 140 through 144 ("ALA3"), 187 through 192 ("ALA4"), 339 through 343 ("ALA5"), 677 through 681 ("ALA6"), 699 through 673 ("ALA7") and 736 through 740 ("ALA8"), using the conventional numbering counting from the N-terminal MET residue as 1. The identity of these native amino acids is shown in Example 2, below.

Analysis of amino acid sequences of the PB2 proteins from numerous other influenza A strains identified the corresponding eight charged clusters in those strains. Such influenza A strains include A/Memphis/8/88, A/Chile/1/83, A/Kiev/59/79, A/Udorn/307/72, A/NT/60/68, A/Korea/426/68, A/Great Lakes/0389/65, A/Ann Arbor/6/60, A/Leningrad/13/57, A/Singapore/1/57, A/PR/8/34 and A/WSN/33. Their sequences are available from GenBank and viral stock may be available from the American Type Culture Collection, Rockville, Md. or are otherwise publicly available. The nucleotides comprising the ALA1, ALA3, ALA4, ALA5 and ALA6 charged clusters are completely conserved in each of these influenza strains.

In the ALA2 charged cluster, the amino acid residue at position 120 is either a D residue or another charged residue, E, in the case of the Chile, NT, Korea, Great Lakes, Ann Arbor, Leningrad, Singapore, PR and WSN strains mentioned above. In the ALA7 charged cluster, the amino acid at position 700 is a G residue in the Kiev strain; in all other strains it is an E residue. In the ALA8 charged cluster, the amino acid residue at position 740 is an N in the Ann Arbor and WSN strains, while the other strains show complete identity with A/LA/2/87 in that charged cluster. Thus, although the A/LA/2/87 strain was used in the examples, any of the foregoing strains could equally have been used. In addition, analyses for charged clusters of amino acids in influenza B and/or influenza C could be readily performed in accordance with the teachings of this invention to create PB2 variant proteins and live recombinant influenza B and influenza C viruses in an manner analogous to that demonstrated here for influenza A. For example, charged clusters corresponding to charged cluster ALA4 and ALA8 in influenza A have been found in two influenza B strains, B/AA/1/66 and B/NY/1/93. Using the teaching disclosed here, one skilled in the art would be able to identify other such charged cluster residues in the other types and strains of influenza.

Additionally, charged clusters in other proteins of influenza viruses may be identified and modified using these techniques. It is specifically contemplated that the M1 proteins of influenza A, B or C can be modified to produced variant M1 proteins which would give rise to immunogenically significant attenuations, thereby enabling production, through known reverse genetics techniques, of live attenuated immunogenic compositions for prophylactic administration in humans. The nucleotide and amino acid sequences of the M proteins from various influenza types and strains are known. See for example, Baylor, *Virol.* 163:618–21 (1988); Markusin, *Virus Res.* 10:263(1988); Cox, *Virology* 167:554–67 (1988) and Buckler-White, *J Virol.* 57:670–700 (1986). One skilled in the art can employ the techniques disclosed herein to identify and modify charged clusters in the influenza M proteins and create recombinant influenza viruses containing such modified M proteins. The nucleotide and amino acid sequences of the NP proteins from several strains of influenza A are known. See for example, Shu, *J Virol* 67:223–29 (1993) One skilled in the art can employ the techniques disclosed herein to identity and modify charged clusters in the influenza NP protein and create recombinant influenza viruses containing such modified NP proteins.

Charged clusters as defined herein can be modified following the teachings here to create temperature sensitive recombinant influenza viruses. Such temperature sensitive recombinant influenza viruses include those containing PB2 variant amino acid sequences, and the encoding RNA sequences, which are responsible for the exhibited temperature sensitivity.

Accordingly, this invention discloses and describes novel RNA and corresponding cDNA sequences encoding PB2 variant proteins. The proteins of this invention comprise variant or modified PB2 sequences in which at least one and up to eight of the charged clusters of wild-type influenza PB2 sequences are modified by substitution of neutral amino acids. The words variant, modified and mutant or mutated are used interchangeably herein. A neutral amino acid is herein defined as uncharged at neutral pH and not disruptive to overall secondary or tertiary structure. Exemplary neutral amino acids include alanine, valine and serine. Alanine is a preferred neutral amino acid.

Such proteins, when incorporated into influenza viruses to create master donor strains of influenza, result in the creation of temperature sensitive mutants useful in the preparation of immunogenic compositions and in the prophylactic treatment of influenza.

The PB2 variant proteins (i.e., the modified PB2 proteins) of this invention can be incorporated into influenza viruses by employing known genetic reassortment or reverse genetic methods. In reverse genetic methods, the native PB2 sequence is replaced with a synthetic gene synthesized in vitro from cDNA which encodes one or more of the charged cluster modifications in the PB2 protein. Helper virus infected cells are transfected with the synthetic PB2 sequence which necessarily encodes the charged cluster modifications. The live virus containing the synthetic sequence can serve as a master donor virus, which, when combined with the wild-type HA and/or NA gene of epidemic (i.e., currently circulating virulent) influenza strains, will result in the production of reassortant influenza viruses ("6:2 reassortants") which can be used as immunogenic compositions in the prophylactic treatment of influenza in human. In an analogous manner, the variant M sequences and/or the variant NP sequences can be incorporated with influenza viruses. The 6:2 reassortant viruses will thus be composed of six genes derived from the master donor strain containing the synthetic sequence or sequences and the HA and NA genes derived from a currently circulating virulent strain of influenza. The method of preparing a 6:2 influenza reassortant virus comprises infecting a cell with the attenuated master donor strain and with a currently-circulating virulent influenza A virus and selecting the reassortant virus by contacting the progeny with an antibody reactive with an epitope on the HA or NA gene of the epidemic strain. Alternatively, reverse genetics techniques can be used to transfect cells with the HA and NA genes from an epidemic strain. The cells are then infected with the master donor strain and 6:2 reassortants selected by antibody mediated selection as described above.

For example, primary chick kidney (PCK) or MDBK cell monolayers are infected with helper virus at a multiplicity of infection (moi) of 1–10 for 1 hour. RNA encoding one or more of the variant PB2, or M1 or NP proteins, of the invention is transfected into the infected cells using the techniques described in Luytjes, supra, Enami and Palese, supra and Enami, supra optionally as modified in Example 4 below. The transcription reaction contains linearized plasmid, each of the deoxyribonucleotides, T3 RNA polymerase and ribonucleoprotein prepared from virus grown in the allantoic cavities of embryonated eggs according to the methods of Parvin and Enami, supra. The mixture is incubated at 37° C. for 45 minutes, resulting in the production of RNA transcripts which are concurrently packaged into RNP complexes. The addition of DNase then eliminates the plasmid and the mixture is introduced into the PCK or MDBK cells, which have been infected with the helper virus and treated with DEAE Dextran. Alternatively, the mixture is introduced into the infected cells by electroporation. Cultures are maintained at the appropriate temperature (e.g. 34° C.) and are harvested about 16–22 hours later. Cell debris is pelleted and the supernatant containing the virus is plaqued on appropriate mammalian cells, for example MDCK cells. The progeny of the plaqued virus can go through subsequent additional plaque passages and is then amplified in the allantoic cavities of embryonated eggs.

More specifically, a host-range mutant of influenza virus A/LA/2/87 has been described. This helper virus contains the PB2 gene derived from the avian virus, A/Mallard/New York/6750/78, and is able to grow productively in avian cells such as PCK cells, but cannot form plaques in mammalian cells such as MDCK. See Clements, J Clin Microbiol 30:655–62 (1992). Replacement of the Mallard PB2 gene in A/LA/2/87 with a transfected, mammalian PB2 sequence allows the virus to plaque in MDCK cells. See Subbarao, J Virol 67:7223–28 (1993). In this way specific alterations in the nucleotide sequence of the PB2 gene can be introduced, by transfecting synthetic RNAs bearing site-directed mutations introduced into the cDNA of the mammalian PB2 sequence, and used for in vitro transcription. The recombinant variant influenza virus so produced will exhibit temperature sensitivity, thereby enabling it to be employed as the master donor strain in the construction of live, attenuated immunogenic compositions for prophylactic administration in humans.

Standard methods may be employed for propagating the recombinant influenza viruses of the invention. Vital stocks can be plaque-purified in primary or established cell cultures, for example, primary bovine or chick kidney cells or MDCK cells. Plaque-purified virus can be further propagated in such cell lines. The cells are cultured typically on plastic tissue culture plates and virus is typically inoculated at a moi of 0.001 to 0.1 and incubated for 2–3 days. Virus stock can alternatively be inoculated into the allantoic cavity of 10–12 day embryonated chicken eggs and incubated for 2–3 days at 33°–37° C.

Testing for attenuation of the recombinant influenza viruses of the invention can be accomplished employing well established in vitro and in vivo assays. In the in vitro assay, the recombinant virus is tested for the presence of the temperature sensitive phenotype, as described in Example 6 below. In vivo reactogenicity of the recombinant influenza viruses can be determined as described in Example 7 below.

Such recombinant modified, variant influenza viruses can also be used in genetic complementation analysis, to map ts lesions of other viruses, in the functional analysis of the role of PB2 in the virus life cycle, and in locating domains of the PB2 protein involved in interactions with viral RNA or other viral proteins such as PB1 or PA.

The modified PB2 proteins of the invention can be expressed recombinantly in different types of cells using the appropriate expression control systems, as is well known in the art, to test protein functionality. The construction of suitable vectors containing the nucleic acids sequences of the invention is likewise well known in the art, as are hybridization assays in which such sequences may be employed. See for example, U.S. Pat. Nos. 4,356,270 issued to Itakura, 4,431,739 issued to Riggs and 4,440,859 issued to Rutter. Other exemplary host cells, promoters, selectable markers and techniques are also disclosed in U.S. Pat. Nos. 5,122,469 issued to Mather, 4,399,216 and 4,634,665 issued to Axel, 4,713,339 issued to Levinson, 4,656,134 issued to Ringold, 4,822,736 issued to Kellems and 4,874,702 issued to Fiers.

The construction of suitable vectors containing the nucleic acid sequences of the invention is accomplished using conventional ligation and restriction techniques now well known in the art. Site specific cleavage is performed by treatment with suitable restriction enzyme(s) under standard conditions, the particulars of which are typically specified by the restriction enzyme manufacturer. Polyacrylamide gel or agarose gel electrophoresis may be performed to size separate the cleaved fragments using standard techniques. Synthetic oligonucleotides can be made using for example, the diethyphosphoamidite method known in the art. Ligations can be performed using T4 DNA ligase under standard conditions and temperatures, and correct ligations confirmed by transforming E. coli with the ligation mixture. Successful transformants are selected by ampicillin, tetracycline or other antibiotic resistance or using other markers as are known in the art.

Such recombinant techniques are fully explained in the literature. See, e.g., Sambrook, MOLECULAR CLONING: A LABORATORY MANUAL, 2d ed. (1989); DNA CLONING, Vol. I and II, D. N. Glover, ed., 1985; OLIGO-NUCLEOTIDE SYNTHESIS, M. J. Gait, ed., 1984; NUCLEIC ACID HYBRIDIZATION, B. D. Hames, ed., 1984; TRANSCRIPTION AND TRANSLATION, B. D. Hames, ed., 1984; ANIMAL CELL CULTURE, R. I. Freshney, ed., 1986; B. Perbal, A PRACTICAL GUIDE TO MOLECULAR CLONING (1984); GENE TRANSFER VECTORS FOR MAMMALIAN CELLS, J. H. Miller, ed., 1987, Cold Spring Harbor Laboratory; Scopes, PROTEIN PURIFICATION: PRINCIPLES AND PRACTICE, 2d ed, Springer-Verlag, New York, 1986 and HANDBOOK OF EXPERIMENTAL IMMUNOLOGY, Vols I–IV, D. M. Weired, ed., 1986. All such publications mentioned herein are incorporated by reference for the substance of what they disclose.

The live recombinant influenza virus variants of the invention may be employed in immunogenic compositions for preventing infection by an influenza virus or the disease state brought about by such infection. To make such immunogenic compositions, cultured cells are co-infected with the live recombinant influenza variant (i.e., the master donor) and an epidemic wild-type strain. Reassortant viruses are harvested and tested for the presence of the temperature sensitivity inducing mutation. Reassortants containing the wild-type HA and/or NA proteins can be selected by exposure to antisera against the surface epitopes encoded by the HA and/or NA proteins from the donor virus. Resultant vital progeny containing the mutated sequences of the invention and the HA and/or NA sequences from the wild-type epidemic influenza strains are used in the preparation of immunogenic compositions. Such immunogenic compositions comprise an immunogenically-inducing effective amount of a recombinant influenza virus variant of the present invention in admixture with a pharmaceutically acceptable carrier or solution. An exemplary pharmaceutically acceptable carrier is saline solution. The composition can be systemically administered, preferably subcutaneously or intramuscularly, in the form of an acceptable subcutaneous or intramuscular solution. More preferably, the composition can be administered intranasally, either by drops, large particle aerosol (greater than 10 microns), or spray into the upper respiratory tract. The preparation of such solutions, having due regard to pH, isotonicity, stability and the like is within the skill in the art. The dosage regimen will be determined by the attending physician considering various factors known to modify the action of drugs such as for example, age, physical condition, body weight, sex, diet, time of administration and other clinical factors. Exemplary dosages range from about 1 to about 1000 $HID_{50}$ (human infectious dose) of the virus.

In practicing the method of prophylactic treatment of this invention, an immunologically-inducing effective amount of an immunogenic composition of the invention is administered to a human patient in need of prophylactic treatment. An immunologically inducing effective amount of a composition of this invention is contemplated to be in the range of about 1–1000 $HID_{50}$, i.e., about $10^5$–$10^8$ pfu (plaque forming units) per dose administered. The number of doses administered may vary, depending on the above-mentioned factors. The route of delivery will preferably be via nasal administration into the upper respiratory tract of the patient.

The invention is further described in the following examples, which are intended to illustrate the invention without limiting its scope.

EXAMPLE 1 cDNA Cloning of A/LA/2/87 Gene

Madin-Darby canine kidney (MDCK) and Madin-Darby bovine kidney (MDBK) cells were obtained from the American Type Culture Collection (ATCC, Rockville, Md.) and grown in Eagle's Modified Essential Medium (EMEM; JRH Biosciences, Lenexa, Kans.) supplemented with 10% fetal bovine serum (JRH), 2 mM L-glutamine (JRH), 100 units/ml penicillin and 0.1 mg/ml streptomycin (Sigma, St. Louis, Mo.), at 37° C. in 5% $CO_2$. Influenza virus A/LA/2/87 (H3N2) was obtained from Dr. L. Potash (DynCorp/PRI, Rockville, Md.), passaged once in MDCK cells at 37° C., then amplified in the allantoic cavity of 10–12 day old, Standard quality, specific pathogen-free (SPF) embryonated chicken eggs (SPAFAS, Norwich, Conn.) at 35° C. as described in Barrett, Growth, Purification and Titration of Influenza Viruses, p. 119–150, B. W. J. Mahy, ed., IRL Press, Oxford, England (1985).

Allantoic fluid from eggs infected with A/LA/2/87 virus was removed and concentrated by centrifugation at 15,000 rpm in an SW28 rotor for 90 minutes at 4° C., then purified by centrifugation on a sucrose step gradient (12–60% sucrose in phosphate-buffered saline) in four 12% steps at 27,000 rpm in an SW28 rotor for 75 minutes at 4° C. Banded virions were disrupted with 1% NP-40. Vital RNA (vRNA) was then extracted, first by treatment with 0.5 mg/ml proteinase K (PK; Amresco, Solon, Ohio) in the presence of 1% sodium dodecyl sulfate (SDS), 50 mM tris (hydroxymethyl) aminomethyl hydrochloride (Tris), pH 7.5, 100 mM NaCl and 1 mM ethylene-diamine-tetra-acetate (EDTA), at 37° C. for 1 hour and then by three successive treatments with an equal volume of phenol/chloroform, and precipitated with 2.5 volumes of ethanol.

After chilling at −20° C. for 1 hour, the RNA containing precipitate was pelleted by centrifugation in an Eppendorf microcentrifuge at 14,000 rpm for 20 minutes, washed with 80% ethanol, dried and resuspended in diethyl pyrocarbonate (DEPC)-treated water to a final concentration of 0.5 mg/ml. Approximately 1 µg of vRNA was hybridized with oligonucleotide PB2003, an oligonucleotide complimentary to the 24 3'-terminal nucleotides of the PB2 gene, based on the sequence of the A/Memphis/8/88 PB2 gene (see Gorman, J Virol 64:4893–4902(1990)), which also contained BamHI and BsmI restriction sites. The sequence of PB2003 is shown in Table 1 below.

First strand cDNA was synthesized using Superscript II reverse transcriptase (Gibco/BRL, Bethesda, Md.) in the reaction buffer provided by the manufacturer, 0.5 mM each deoxy-nucleotide triphosphate (dNTPs; Promega, Madison, Wis.), and 2 units/µl RNAsin (Promega), at 42° C. for 2 hours. The cDNA was purified by phenol/chloroform extraction, and chromatographed over an S-300 HR microcolumn (Pharmacia, Piscataway, N.J.). The cDNA was then amplified, using the polymerase chain reaction (PCR), in two segments, both of which comprised the unique NcoI site at position 1229. The C-terminal clone was prepared using oligonucleotide primers PB2003 and PB2005 (vRNA sense, positions 1257–1276; see Table 1 for the sequence of PB2005). The N-terminal clone was made using primers PB2002 (vRNA sense, containing an XbaI restriction site, the T3 promoter sequence, and 28 nts from the 5' end of PB2 vRNA) and PB2004 (mRNA sense, positions 1126–1146). The sequences of PB2002 and PB2005 are shown in Table 1.

PCR was carried out in a Perkin Elmer (Norwalk, Conn.) thermal cycler, in 1× PCR buffer II (Perkin Elmer) containing 2 mM $MgCl_2$, 0.2 mM dNTPs, 0.2 µM each primer, and 2.5 units Taq polymerase, by performing 50 cycles of denaturation at 94° C. for 1 minute, annealing at 40° C. for 2 minutes, and extension at 72° C. for 3 minutes, followed by incubation at 72° C. for 30 minutes. The PCR-generated fragments were phenol/chloroform extracted, ethanol precipitated, and electrophoresed in a 1% low-melting point agarose gel (FMC, Rockland, Me.) for 100 volt-hours in 1× TAE buffer (40 mM Tris-acetate, 1 mM EDTA, pH 8.0). The DNA fragments of the expected sizes (1.29 kb for the N-terminal fragment, and 1.24 kb for the C-terminal fragment) were excised from the gel, the gel slice was melted, and the DNA extracted using the "QN+" procedure as described (Langridge, Anal Biochem 103:264–71 (1980)). An aliquot of each purified DNA was used for ligation to the pCRII TA-cloning vector (InVitrogen, San Diego, Calif.) using T4 DNA ligase (New England Biolabs, Beverly, Mass.). An aliquot of the ligation mixture was used to transform competent E. Coli DH5α cells (Gibco/BRL, Bethesda, Md.). Individual colonies were screened for the presence of the inserts by standard techniques.

Sequencing of the PB2 gene inserts was performed, using primers whose sequence was based on that of the A/Memphis/8/88 PB2 gene, by dideoxy chain termination sequencing of double-stranded plasmid DNA with Sequenase (USB, Cleveland, Ohio). The sequence of two independent clones for each fragment was determined and found to be identical except for a one nucleotide deletion in one of the N-terminal clones, which was discarded since it is predicted to cause a frameshift mutation in the open reading frame encoding PB2. As expected, the sequence was highly homologous to that of the A/Memphis/8/88 PB2 gene, with only 11 nucleotide and 3 amino acid differences. The A/Memphis/8/88 PB2 sequence is disclosed in Gorman, *J Virol* 64:4893–4902 (1990). Sequence differences between A/Memphis/8/88 (as reported in GenBank) and A/LA/2/87 PB2 genes were found at nucleotide positions (counting from the first nucleotide of the cRNA(+) sense strand): 80 (G in Memphis/8/88 and A in A/LA/2/87), 81 (A in Memphis/8/88 and G in A/LA/2/87), 306 (T in Memphis/8/88 and C in A/LA/2/87), 338 (A in Memphis/8/88 and C in A/LA/2/87), 504 (C in Memphis/8/88 and A in A/LA//87), 505 (A in Memphis/8/88 and C in A/LA/2/87), 543 (T in Memphis/8/88 and G in A/LA/2/87), 886 (C in Memphis/8/88 and A in A/LA/2/87), 887 (A in Memphis/8/88 and C in A/LA/2/87), 990 (G in Memphis/8/88 and A in A/LA/2/87), 1164 (A in Memphis/8/88 and G in A/LA/2/87), 1179 (T in Memphis/8/88 and C in A/LA/2/87) and 1929 (T in Memphis/8/88 and C in A/LA/2/87). Resequencing of a small portion of the Memphis/8/88 cDNA uncovered two errors, at positions 80 and 81, in the GenBank sequence; the sequence at these positions is the same as that of A/LA/2/87. Three of the nucleotide differences resulted in amino acid differences in A/LA/2/87, at amino acid positions 104, 160, and 287.

The full-length PB2 cDNA was then re-constructed by digestion of the C-terminal clone with BamHI and NcoI, and of the N-terminal clone with XbaI and NcoI. The DNA fragments released by the digestion were gel purified using the QN+ procedure and ligated into a BamHI/XbaI-digested pUC19 standard cloning vector.

TABLE 1

Oligonucleotide sequences Used in Examples 1, 2 and 5.
Sequences are listed 5' to 3'.

| | |
|---|---|
| PB2002 | GCGCGCTCTAGAATTAACCCTCACTAAAAGTAGAAACAAGGTCGTT TTTAAACTAT [SEQ ID NO:1] |
| PB2003 | GCGCGCGGATCCGAATGCGAGCAAAAGCAGGTCAATTA TATTC [SEQ ID NO:2] |
| PB2004 | GGGAAAAGGGCAACAGCTATA [SEQ ID NO:3] |
| PB2005 | CACCTCTAACTGCTTTTATC [SEQ ID NO:4] |
| PB2006 | GAAAAAGCACTTTTGCATC [SEQ ID NO:5] |
| n2pb2.4 | AAGAGCCACAGTATCAGCAG [SEQ ID NO:6] |
| ALA1 | GTATCTCGCGAGTGCGAGACTGCGACATCAGGTTCCGTAGTTCAG CTATAGCTTCCATACTG [SEQ ID NO:7] |
| ALA2 | GGTTCCATGTTTTAAAGCTTCAACAGCGTCAAAATA AGTCTTGTAG [SEQ ID NO:8] |
| ALA3 | CCAGGGTTTATGTCTACAGCTGCGGCTATTTTG ACTTGATTTC [SEQ ID NO:9] |
| ALA4 | GCAATCTCGGAGTTCTTCAGCTGCCTCTTTGGTTA TTGTTAATTG [SEQ ID NO:10] |
| ALA5 | CAAGCGGGTCCTCAATCGCAGCTGAGGAAGAAGT GCTTACAGGC [SEQ ID NO:11] |
| ALA6 | CCGGATGTGCTTGCAGCTGGGGCTTCAATTAAAGTGCC [SEQ ID NO:12] |
| ALA7 | GCTTAATGCTGGTCCGTACGCTGCGTCTTCCTTACCTAG [SEQ ID NO:13] |
| ALA8 | GCTAGAGTCCCGTTTTCTGGCCATTACCAACACCACG [SEQ ID NO:14] |

EXAMPLE 2

Mutagenesis of the PB2 cDNA

We defined a charged cluster as four or five positively or negatively charged amino acids in a sequence of five consecutive amino acids and we identified eight charged clusters in the amino acid sequence of the influenza A/LA/2/87 PB2 protein. Using the cDNA cloned in Example 1, we constructed eight PB2 variant cDNAs containing specific, site-directed modifications as follows.

A summary of the positions of the clusters and the amino acid modifications and restriction enzyme sites introduced into the cloned PB2 cDNAs from Example 1 is presented in detail below. In all cases except one, only the positively charged amino acids (R or K) in the cluster were modified by the substitution of nucleotides encoding a neutral amino acid residue, alanine. This was to minimize the possibility of a spontaneous reversion, since any codon for the neutrally-charged alanine (GCA, GCC, GCG, or GCU) can be mutated back to negatively-charged aspartate (GAC or GAU) or glutamate (GAA or GAG) amino acid residues by a single nucleotide change. In the case of ALA6, in which the cluster is composed of only negatively charged amino acids, the two D residues and the second E residue were modified by substitution of nucleotides encoding for alanine. The ALA8 mutation introduced is coincident with part of the proposed nuclear localization signal and mutation to glutamine at the same position in the PB2 protein of the A/WSN/33 strain of influenza A was shown to result in production of PB2 protein equally distributed between the nucleus and the cytoplasm of BHK cells expressing the recombinant protein. See Mukaigawa and Nayak, *J Virol* 65:245–253 (1991). In all cases, other translationally silent mutations were made in order to introduce restriction enzyme (RE) changes for the purpose of tracing the various alleles.

PB2 cDNAs containing the ALA1 and ALA5 modifications were generated by cassette mutagenesis using fragments amplified by the PCR. A primer (ALA1 or ALA5, see Table 1 for their sequences) which contained the sequence of a nearby unique restriction site, as well as the sequence of the desired substitution, was used in conjunction with a primer of opposite sense distal to another unique restriction site. PB2 cDNAs containing the ALA2, ALA3, ALA4, ALA6, ALA7, and ALA8 were generated using the Chameleon Site Directed Mutagenesis Kit (Stratagene, La Jolla, Calif.).

The amino acid changes made in the LA PB2 mutants were as follows. The ALA1 mutation consisted of changing the wild type amino acids R and K at wild type amino acid positions 3 and 5 to alanine in the five amino acid cluster beginning with E at wild type amino acid position 2 and introducing an Sfc1 RE site to trace the allele. The ALA2 mutation consisted of changing the wild type amino acids K and R at wild type amino acid positions 121 and 124 to alanine in the five amino acid cluster beginning with D at wild type amino acid position 120 and introducing an HindIII RE site to trace the allele. The ALA3 mutation consisted of changing the wild type amino acids R, R and R at wild type amino acid positions 142, 143 and 144 to alanine in the five amino acid cluster beginning with K at wild type amino acid position 140 and introducing an Pvu11 RE site to trace the allele. The ALA4 mutation consisted of changing the wild type amino acids K and K at wild type amino acid positions 189 and 190 to alanine in the six amino acid cluster beginning with K at wild type amino acid position 187 and introducing an Pvu11 RE site to trace the allele. The ALA5 mutation consisted of changing the wild type amino acids K and R at wild type amino acid positions 339 and 340 to alanine in the five amino acid cluster beginning with K at wild type amino acid position 339 and introducing an Pvu11 RE site to trace the allele. The ALA6 mutation consisted of changing the wild type amino acids D, D and E at wild type amino acid positions 678, 680 and 681 to alanine in the five amino acid cluster beginning with E at wild type amino acid position 677 and introducing an Pvu11 RE site to trace the allele. The ALA7 mutation consisted of changing the wild type amino acids R and R at wild type amino acid positions 702 and 703 to alanine in the five amino acid cluster beginning with K at wild type amino acid position 699 and introducing an BsiW1 RE site to trace the allele. The ALA8 mutation consisted of changing the wild type amino acid K at wild type amino acid positions 736 to alanine in the five amino acid cluster beginning with K at wild type amino acid position 736 and introducing an Msc1 RE site to trace the allele.

EXAMPLE 3

Preparation of viral RNP

Viral ribonucleoprotein (RNP) was purified from A/PR/8/34 virus grown in SPF eggs using the protocol described in Parvin, *J Virol* 63:5142–5152(1989), with certain modifications, as disclosed below.

Six to seven hundred SPF eggs were injected with approximately $10^4$ pfu of the influenza A/PR/8/34 virus and incubated at 35° C. for 2 days. After chilling to 4° C. overnight, allantoic fluid was harvested and concentrated approximately 10-fold using an Amicon Hollow Fiber Cartridge (Type HIP100-20) and an Amicon LP-1 pump. Virus was pelleted by centrifugation in a SW28 rotor at 25,000 rpm for 90 minutes at 4° C., resuspended in 100 mM NaCl, 10 mM Tris-HCl, pH 7.5, 10 mM EDTA (NTE buffer), and re-pelleted twice through a 30% sucrose cushion (25,000 rpm in a SW28 rotor for 2.5 hours, then 36,000 rpm in a SW50.1 rotor for 90 minutes).

The viral pellet was resuspended in 0.1M Tris, pH 8.1, 0.1M KCl, 5 mM $MgCl_2$, 5% glycerol, 1.5% Triton-N101, 10 mg/ml lysolecithin (freshly added), and 1.5 mM dithiothreitol (DTT), to a final protein concentration of 3 mg/ml, and incubated at 37° C. for 30 minutes. Disrupted virus was concentrated on an Amicon Centriprep-10 concentrator for 1–3 hours at 3000 rpm in a Beckman J-6B centrifuge. Viral cores were purified on a three-layer glycerol step gradient (33%, 50%, and 70% glycerol) centrifuged in a SW50.1 rotor at 45,000 rpm, 4° C., for 4 hours. Fractions of 0.3 ml were harvested from the gradient and analyzed by SDS-polyacrylamide gel electrophoresis (SDS-PAGE).

Fractions enriched in NP protein were pooled and centrifuged through a CsCl/glycerol step gradient (three layers: 1.5M CsCl/30% glycerol, 2.0M CSCl/35% glycerol, and 2,5M CsCl, 40% glycerol), in a SW50.1 rotor at 45,000 rpm for 24 hours at 4° C. Again, fractions enriched in NP protein were pooled, and dialyzed to a final buffer composition of 50% glycerol, 50 mM Tris pH 7.5, 100 mM NaCl, 10 mM $MgCl_2$, and 1 mM DTT using dialysis tubing with a molecular weight cut-off of 50,000 daltons. The protein concentration of various RNP preparations ranged from 1 to 2 mg/ml. RNPs were stored at −80° C. The activity of the RNP was determined by NA rescue using the WSN-HK helper virus according to the method of Enami, *Proc Nat Acad Sci USA* 87:3802–3805 (1990) and the protocol outlined below, except that 0.1 µg/µl RNP was used and the virus obtained was plaqued on MDBK cells in the absence of trypsin. The transfection yield was usually 5–10×$10^4$ pfu.

EXAMPLE 4

Transfection of the PB2 Variant cDNAs and Rescue of Recombinant PB2 Virus

Wild-type influenza A/LA PB2 cDNA and the eight influenza A/LA PB2 cDNA variants constructed in Example 2 were rescued into influenza virus using a modified version of the reverse genetics protocol originally described by Palese and co-workers (see, for example, Enami and Palese, *J Virol* 65:2711–13(1991)) and employing a host-range mutant PB2 helper virus, as described by Murphy and colleagues in Clements, *J Clin Microbiol* 30:655–662(1992) and Subbarao, *J Virol* 67:7223–8(1993). The PB2 host-range helper virus is a single gene reassortant virus containing the PB2 gene from A/Mallard/NY/6750/78 and the remaining seven genes from A/LA/2/87. It was obtained from Dr. L. Potash (DynCorp/PRI, Rockville Md.) and grown in SPF eggs.

This PB2 helper virus had been used previously for rescue by transfection of primary chick kidney (PCK) cells (see Subbarao, *J Virol* 67:7223–8(1993)), since the virus is a host-range mutant which can grow productively in PCK cells but does not form plaques in mammalian cells. See Clements, *J Clin Microbiol* 30:655–662 (1992). Surprisingly, we found that the mammalian cell line, MDBK, could be infected with the virus and could support the expression of a transfected reporter gene (chloramphenicol acetyl transferase, CAT) which is dependent on influenza polymerase function for expression (IVACAT). See Luytjes, *Cell* 59:1107–1113(1989). Instead of PCK cells we therefore used MDBK cells for PB2 rescue experiments.

In addition, we employed an improved transfection method which uses electroporation of MDBK cells and yields equal or greater numbers of transfectant viruses with a 10-fold reduction in replication of helper virus compared to the previously described DEAE-dextran transfection procedure (See Li, *Virus Res*, in press and U.S. Ser. No. 08/316,049 filed Sep. 30, 1994, herein incorporated by reference). The electroporation technique also appeared to eliminate another source of background, namely, the rescue of the RNA encoding PB2 from A/PR/8/34, which is present in low amounts in the RNP preparation.

MDBK cells were obtained from the ATCC, Rockville, Md. Sub-confluent monolayers of MDBK cells (one 60 mm dish per transfection) were infected with the helper virus diluted in phosphate-buffered saline (PBS; JRH BioSciences, Lenexa, Kans.) to give a multiplicity of infection (moi) of 5, for 1 hour at room temperature. The infected cells were removed from the dish by applying 0.4 ml of pre-warmed (37° C.) 0.5% trypsin (JRH) for 2 minutes at room temperature. The trypsin was inactivated by adding 2 mg soybean trypsin inhibitor (Sigma) in PBS containing $Mg^{+2}$ and $Ca^{+2}$ (JRH). The infected cells were pelleted at 2000 rpm in a Beckman tabletop clinical centrifuge for 5 minutes at room temperature, and resuspended in 0.3 ml PBS. The cells were transferred to an electroporation cuvette (0.4 cm gap, Bio-Rad, Hercules, Calif.). vRNA-sense RNP was prepared by in vitro transcription of the BsmI-linearized PB2 cDNA (2 µg per transcription) with T3 polymerase (2 units/µl, Stratagene, LA Jolla, Calif.) in the presence of 0.5 mM each nucleotide triphosphate (Promega, Madison, Wis.), 1 unit/µl RNAsin (Promega), and 0.2–0.4 µg/µl purified RNP protein. Transcriptions were incubated at 37° C. for 45 minutes, followed by treatment with RQ1 DNase (Promega) at 37° C. for 5 minutes. The RNP mixture was added to the infected cells in the cuvette and immediately electroporated with one pulse at 250 mV, 500 µF using a Bio-Rad (Hercules, Calif.) Gene Pulser. The electroporated cells were then re-plated in 2 ml of MEM (JRH) containing 1% bovine serum albumin (BSA; Gibco/BRL, Grand island, N.Y.) and 1.25 µg/ml L-(tosylamido-2-phenyl) ethyl chloromethyl ketone (TPCK)-treated trypsin (Worthington Biochemical Corp., Freehold, N.J.) and incubated overnight at 34° C.

The supernatant was harvested and used undiluted to infect confluent monolayers of MDCK cells in 10-cm dishes (two per transfection), which were then overlaid with 0.8% agarose in L-15 medium (JRH) containing 2.5 µg/ml TPCK-trypsin and incubated at 34° C. for three days. Plaques were picked into 0.5 ml of MEM/1% BSA, dispersed with a pipette, and 0.1 ml of the plaque dispersion was used to infect MDCK cells in 24-well dishes. The infected MDCK cells were incubated at 34° C. for 2–3 days and screened for recombinant virus as described in Example 5 below.

EXAMPLE 5

RT/PCR Screening for Recombinant Virus

Supernatants from wells showing cytopathic effects (CPE), i.e., cell elongation and rounding, followed by cell detachment and death, were harvested and treated with RQ1 DNase at 37° C. for 10 minutes to prevent carryover of trace amounts of input cDNA. vRNA was prepared by PK treatment of the medium followed by phenol/chloroform extraction and ethanol precipitation as described in Example 1 above. One third of the RNA was used for RT/PCR screening, employing the primers n2pb2.4 and PB2006 (see Table 1 for the sequences of these primers). These primers are able to amplify a short region of the PB2 gene from the three strains used in these experiments (A/LA/2/87, A/PR/8/34, or A/Mallard/NY/6750/78). First strand cDNA was synthesized using Superscript II reverse transcriptase (Gibco/BRL, Bethesda, Md.) in the reaction buffer provided by the manufacturer, 0.1 mM each deoxy-nucleotide triphosphate (dNTPs; Promega, Madison, Wis.), 1 µM $n^2pb2.4$ primer, and 2 units/ml RNAsin (Promega), at 42° C. for 30 minutes. The reaction mixture was adjusted to 1× PCR buffer II (Perkin Elmer), 2 mM MgCl2, 0.2 mM dNTPs, 0.2 µM each primer, and 2.5 units Taq polymerase. PCR was carried out in a Perkin Elmer (Norwalk, Conn.) thermal cycler. Thirty-five cycles of denaturation at 94° C. for 1 minute, annealing at 50° C. for 1 minute, and extension at 72° C. for 2 minutes, were performed, followed by incubation at 72° C. for 30 minutes.

The PCR fragments generated using these primers were characterized by digestion with HinfI (New England Biolabs, Beverly, Mass.), which produces different sized digestion products that are diagnostic for the PB2 genes of the three strains as shown in Table 3 below.

TABLE 3

| PB2 RT/PCR HinfI digestion fragment sizes (bp) | | |
|---|---|---|
| A/LA/2/87 | A/PR/8/34 | A/Mallard/NY/78 |
| 331 | 176 | 360 |
| 149 | 163 | 80 |
| 56 | 129 | 68 |
|  | 56 | 28 |
|  | >12 |  |

PB2 variant viruses from plaques that were identified as having the variant PB2 RNA sequences were plaque-purified in MDCK cells, passaged once in MDCK cells at 34° C. (in MEM+trypsin, 2–3 days), re-screened by RT/PCR and HinfI restriction analysis as above and then grown in SPF eggs (SPAFAS) at 35° C., except for virus incorporating the ALA4 mutation which was grown in SPF eggs (SPAFAS) at 33° C. The RT/PCR demonstrated that six of the eight PB2 variant influenza viruses were successfully transfected and rescued using the foregoing techniques (ALA1, ALA4, ALA5, ALA6, ALA7 and ALA8). ALA2 and ALA3 were not rescued after several attempts, and thus are likely to encode PB2 proteins that are biologically inactive in MDCK cells.

EXAMPLE 6

Determination of Temperature Sensitivity

Stocks of the PB2 variant viruses from Example 5 above were titrated by plaque assay in MDCK cells at 34° C. (permissive temperature) in a $CO_2$ incubator, or at 37°, 38°, 39° or 40° C. in Nalgene bio-containers (Nalge, Rochester, N.Y.) submerged in water baths whose temperatures were tightly regulated by Lauda constant temperature immersion circulators (Fisher Scientific, Sunnyvale, Calif.). The water baths maintained the desired temperatures within a 0.1° C. range. The water-tight containers were purged with 5% $CO_2$, 21% $O_2$, 74% $N_2$ (BioBlend; Altair, San Ramon, Calif.) before closing. Shut-off temperature was defined as the lowest temperature at which a 100-fold or greater reduction in the efficiency of plaquing (EOP) is observed, relative to that observed at 34° C.

A virus was defined as being temperature sensitive if the plaque size was reproducibly reduced at elevated temperatures and/or if the EOP was reduced 10-fold or more at 39° C. EOP and plaque morphology were analyzed at temperatures ranging from 37° to 40° C. The EOP of the parental A/LA/2/87 virus or of the wild-type transfectant (isolate LA 36–8.1) varied less than 2-fold over this range. The results are shown in Table 4 below.

TABLE 4

Phenotypes of PB2 ALA mutant viruses in MDCK cells

| virus | titer in eggs ($\log_{10}$ pfu/ml) | plaque size[1] at 34° C. | plaque size at 39.5° C. | shut-off temperature |
|---|---|---|---|---|
| A/LA/2/87 | 8.4 | large | large | >40° C. |
| LA 36-8.1 | 8.4 | large | large | >4° C. |
| ALA1 | 7.0 | small | tiny | 39° C. |
| ALA4 | 7.5 | small | — | 38° C. |
| ALA5 | 7.8 | large | large | >40° C. |
| ALA6 | 7.8 | small | tiny | 40° C. |
| ALA7 | 7.8 | large | small | 40° C. |
| ALA8 | 8.0 | large | small | 40° C. |

[1]plaque diameter (after 3 days incubation): large = 2–3 mm; small = 1–2 mm; tiny = ≦1 mm

EXAMPLE 7

Reactogenicity of PB2 Variant Viruses in Ferrets

Ferrets are the animal model of choice for testing the reactogenicity of candidate influenza vaccine strains, since they show several signs of influenza infection which are shared with humans, such as fever, coryza, sneezing, and lethargy.

Ten to twelve week old, male, castrated ferrets, pre-screened for antibodies to influenza and treated with Penicillin for 7 days (30,000 units per day) were obtained from Triple F Farms (Sayre, Pa.). Ferrets were anaesthetized with diethyl ether and infected intranasally with approximately $10^8$ $EID_{50}$ virus in an innoculum of 1 ml (0.5 ml in each nostril). The body temperature of the infected ferrets was determined rectally twice daily for three days. The normal body temperature of uninfected ferrets is 39° C. (102.2° F.). Fever is defined as a temperature of 39.75° C. (103.5° F.) or above. After 3 days the ferrets were euthenized via heart puncture with sodium pentobarbital (130 mg/ferret) and the lungs and nasal turbinates were removed. Tissue suspensions (10% wt./vol.) were prepared by homogenization in Hank's balanced saline solution (HBSS, Gibco/BRL, Bethesda, Md.) containing 2× Basal Eagle Media (BME) Amino Acids, 2× BME Vitamins, 4 mM L-Glutamine, and 0.05 mg/ml Gentamycin sulfate (all supplements from Gibco/BRL). Viral titers were determined using the $EID_{50}$ assay, as described in Barrett, Growth, Purification and Titration of Influenza Viruses, p. 119–150, B. W. J. Mahy, ed., IRL Press, Oxford, England (1985).

The two most attenuated PB2 mutants, ALA1 (isolate 49-14.1) and ALA4 (isolate 65-31.1), were used to infect groups of three ferrets each. As controls, three ferrets were also infected with a transfectant virus containing the wild-type LA PB2 gene (isolate LA 36-8.1 was used as control for ALA1, and LA 36-9.1 was used as control for ALA4). The results are shown in Table 6a and 6b below. ALA1 was not significantly attenuated, since it replicated to identical levels in the turbinates, and induced an identical rise in temperature, as did the wild-type transfectant. However, ALA4 did not cause fever in any of the 3 ferrets infected, and replicated to lower titers in the nasal turbinates. These results demonstrate that a ts virus generated by clustered charged-to alanine mutagenesis of the PB2 gene (ALA4) has a phenotype that has utility in generating vaccine candidates with an attenuated character.

TABLE 6a

Reactogenicity of ALA1 in Ferrets

| virus | dose ($\log_{10}$ $EID_{50}$) | nasal turbinate titer ± SE ($\log_{10}EID_{50}$ per g) | lung titer ($\log_{10}EID_{50}$ per g) | peak temperature ± SE (°C.) | duration of fever |
|---|---|---|---|---|---|
| LA 36-8.1 | 8.5 | 6.77 ± 0.15 | ≦3.0 | 40.85 ± 0.10 | 48 hrs. |
| ALA1 49-14.1 | 8.5 | 6.23 ± 0.77 | ≦3.0 | 40.78 ± 0.17 | 48 hrs. |

TABLE 6b

Reactogenicity of ALA4 in Ferrets

| virus | dose ($\log_{10}$ $EID_{50}$) | nasal turbinate titer ± SE ($\log_{10}EID_{50}$ per g) | lung titer ($\log_{10}EID_{50}$ per g) | peak temperature ± SE (°C.) | duration of fever |
|---|---|---|---|---|---|
| LA 36-9.1 | 8.0 | 5.83 ± 0.09 | ≦3.0 | 40.41 ± 0.08 | 48 hrs. |
| ALA4 65-31.1 | 7.6 | 4.16 ± 0.61 | ≦3.0 | 39.34 ± 0.34 | None |

What is claimed is:

1. A recombinant RNA sequence encoding an influenza PB2 protein, wherein said RNA sequence comprises a mutation selected from the group consisting of the mutations set forth as ALA1, ALA4, ALA6, ALA7 and ALA8.

2. A recombinant influenza virus comprising the recombinant RNA sequence of claim 1.

3. A recombinant PB2 protein which is encoded by the recombinant RNA sequence of claim 1.

4. A recombinant DNA sequence which comprises a complementary DNA sequence of the recombinant RNA sequence of claim 1.

* * * * *